United States Patent [19]

Andringa et al.

[11] Patent Number: 5,057,007
[45] Date of Patent: Oct. 15, 1991

[54] LOW $NO_x$ ATMOSPHERIC GAS BURNER

[75] Inventors: Willem W. Andringa, Beekbergen; Terence A. Devlin, Apeldoorn; Hermanus J. Meuleman, Kaliumstraat, all of Netherlands

[73] Assignee: Remeha Fabrieken, Netherlands

[21] Appl. No.: 422,154

[22] Filed: Oct. 16, 1989

[30] Foreign Application Priority Data

Jan. 6, 1989 [NL] Netherlands ............... 8900030

[51] Int. Cl.⁵ ............................................. F23D 14/12
[52] U.S. Cl. .................................... 431/328; 431/326; 431/329; 126/92 B; 126/91 R
[58] Field of Search ................ 431/328, 329, 326; 126/91 R, 91 A, 92 B

[56] References Cited

U.S. PATENT DOCUMENTS

| | | | |
|---|---|---|---|
| 3,028,909 | 4/1962 | Faure | 158/132 |
| 3,173,470 | 3/1965 | Wright | 431/328 |
| 3,403,965 | 10/1968 | Dreisziger | 431/328 X |
| 3,790,333 | 2/1974 | Padovani et al. | 126/92 B X |
| 4,133,632 | 1/1979 | Nakano | 431/328 |
| 4,652,236 | 3/1987 | Viesmann | 431/350 |
| 4,887,963 | 12/1989 | LeMer | 431/328 X |

FOREIGN PATENT DOCUMENTS

| | | |
|---|---|---|
| 0191722 | 7/1986 | European Pat. Off. . |
| 0195360 | 9/1986 | European Pat. Off. . |
| 8626548 | 11/1986 | Fed. Rep. of Germany . |
| 1037232 | 9/1953 | France . |
| 59-21909 | 4/1984 | Japan . |
| 209621 | 1/1924 | United Kingdom . |

OTHER PUBLICATIONS

E. J. Pearson et al., "Fully Premixed Natural Gas Burners for Use in High Thermal Efficiency Domestic Burners", 1983 International Gas Research Conference, London, IGRC/C24-83, 13-16 Jun. 1983, pp. 1-12.
Patent Abstracts of Japan, vol. 8, No. 112 (M-298) (1549) May 25, 1984.
K. J. A. Hargreaves et al., "Advanced Combustion Systems for High Efficiency Domestic Appliances", Lecture Presented by the Authors at a Seminar Given in London in 1983.

Primary Examiner—Larry Jones
Attorney, Agent, or Firm—Peter L. Michaelson

[57] ABSTRACT

A low $NO_x$ atmospheric gas burner is provided, which includes at least one burner tube having a plurality of gas outlet orifices terminating in a burner bed, and a plurality of plates disposed above the burner tube within the reach of the flame, which plates lower the temperature and effect a stepped combustion. According to the invention, the plates extend parallel to, and on opposite sides of, the orifices provided in the burner tube, and the orifices are arranged in a line parallel to the burner axis. The plates are connected direct to the burner tube substantially throughout the entire length of their lower edges.

12 Claims, 2 Drawing Sheets

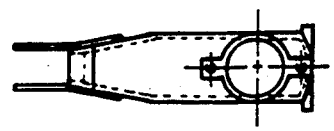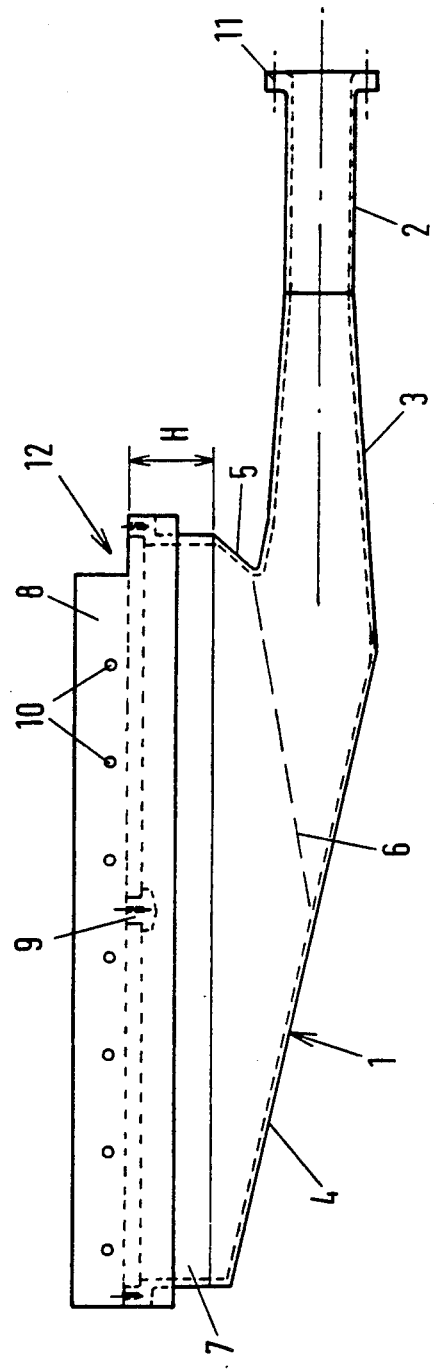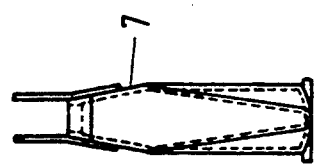

LOW NO$_x$ ATMOSPHERIC GAS BURNER

BACKGROUND OF THE INVENTION

The invention relates to a low NO$_x$ atmospheric gas burner comprising at least one burner tube having a plurality of gas outlet orifices terminating in a burner bed, and a plurality of plates disposed above the burner tube within the reach of the flame, said plates lowering the temperature and also effecting a stepped combustion, a low NO$_x$ production being thus achieved.

DESCRIPTION OF THE PRIOR ART

A similar atmospheric gas burner is known from European patent application 0 195 360, comprising a large number of plates which exend at right angles to the burner axis, whose shape is adjusted to that of the burner tube and whose lower edge in each case is connected to the burner tube only locally so that the atmosphere to the one side of the plates communicates with the atmosphere to the other side.

SUMMARY OF THE INVENTION

It is an object of the present invention to simplify and improve that known arrangement, so that a very uniform flame picture will result, while furthermore the production of noise is limited.

To this effect, a low NO$_x$ atmospheric burner of the type described in the preamble is characterized, according to the present invention, in that the plates extend parallel to, and on opposite sides of, the orifices disposed in the burner, said orifices being arranged in a line parallel to the burner axis, and said plates being connected directly to the burner tube substantially throughout the entire length of their lower edges. Thus a gas burner is obtained that is very simple and yet functions excellently.

To improve flame stability small air supply holes may be provided in the plates mentioned.

To ensure that the flame transfers correctly when the burner is ignited, each of the plates may be provided with at least one aperture.

If the gas burner comprises a substantially horizontal duct which gradually widens away from the gas supply inlet, is shaped to deflect the gas flow in an upward direction and at its outlet end has a width equal to the desired width of the burner or the burner bed, the burner tube further having a constriction just upstream of its outlet end, as is known, for instance, from European patent application 0 191 722, in a further embodiment of the present invention, a distributor plate may be provided at, or just upstream of, the constriction in the burner tube, which has the effect of providing a uniform flame picture.

If the burner tube is further provided in known manner with a bottom surface that slopes upwardly, the sidewalls adjacent to the bottom surface may slope outwardly from the bottom to a maximum width that is uniform throughout the entire length of the burner tube, which provides for a further improvement in the uniformity of the flame picture.

That uniformity is further enhanced by making the distance from the cross-section of equal maximum width to the top of the burner bed so large as to ensure a straight flow of the combustion gas mixture to the burner orifices.

In a further embodiment of the invention, when the burner orifices are formed by plane and corrugated plates or strips, as known per se from I.G.R.C./C24-83 (a 1983 International Gas Research Conference publication), the height of the corrugated strips is smaller than that of the plane strips. The plane strips may in that case extend vertically to above the corrugated strips.

The gas burner may be further provided with at least one additional cooling member which consists of heat-resistant fine-meshed gauze or expanded material. This heat-resistant material may be attached to the plates.

An additional advantage of this combination of stepped combustion and cooling is that the risk of incomplete combustion is much smaller than in the conventional free arrangement of cooling members, where a small change in position causes cooling to take place in a wrong phase of combustion, the result being incomplete combustion. This problem is decidedly substantially mitigated in the present construction by virtue of the fact that, due to the construction, the primary combustion is clearly separated from the secondary combustion.

BRIEF DESCRIPTION OF THE DRAWINGS

Several embodiments of the invention will now be described, by way of example, with reference to the accompanying drawings in which FIG. 1 is a diagrammatic side-elevational view of a gas burner according to the invention;

FIG. 2 is a top view of an arrangement according to the invention as shown in FIG. 1;

FIG. 3 is a left-hand side-elevational view of the arrangement according to FIG. 1;

FIG. 4 is a right-hand side-elevational view of the arrangement according to FIG. 1;

DESCRIPTION OF THE PREFERRED EMBODIMENTS

Figures 5, 6, 7, 8:
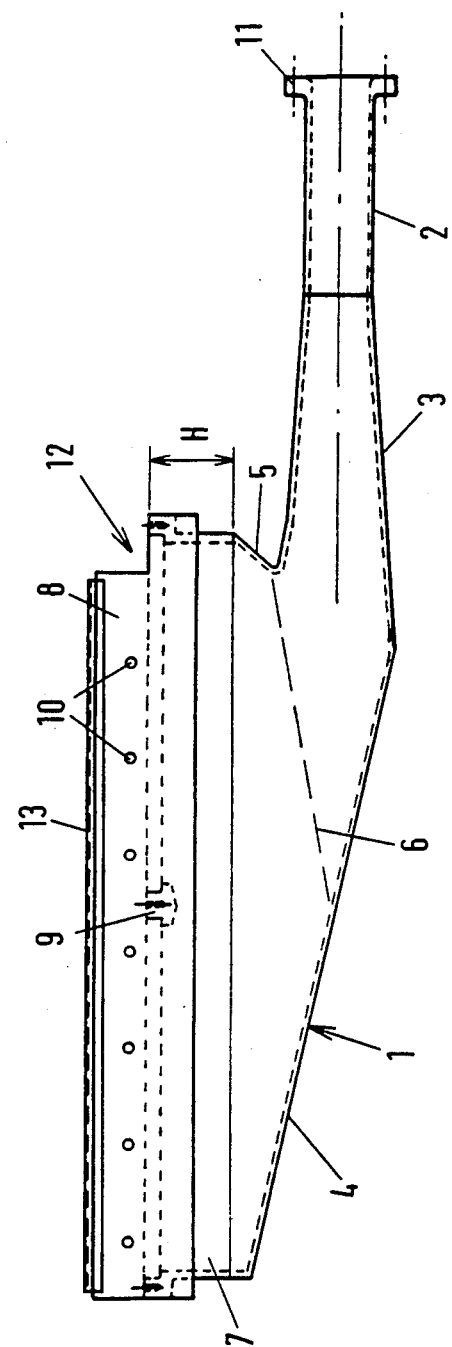
FIG. 5, 6, 7 and 8 show cross-sectional and elevational views similar to FIGS. 1-4, but illustrate a different embodiment.

Referring to the drawings, there is shown a low NO$_x$ atmospheric gas burner which comprises a burner tube 1, the inlet portion of which constitutes a mixing tube portion 2, which connects to a diffuser portion 3. The burner tube 1 proper has a bottom 4 and, on the opposite side, a constriction portion 5. A distributor plate 6 extends between these two portions 4 and 5. A narrowing portion 7 extends upwardly from this burner tube part, at the top of which narrowing portion, not shown, gas outlet orifices are provided, formed by plane and corrugated strips and together constituting a burner bed. Abutting with the upper edges of the walls forming said narrowing portion are two parallel plates 8 which lower the temperature and contribute to a stepped combustion. As is shown in the drawings, the plane and corrugated strips (not shown) can be supported not only at their respective ends, but also in the middle portion by means of a support 9.

To ensure that the flame transfers correctly when the gas burner is ignited, apertures 12 are provided in the plates 8.

To improve the stability of the flame the plates 8 are provided with small air supply holes 10 uniformly spaced apart.

The tapering course of the burner tube walls adjacent to the bottom 4 (shown in FIG. 3) ensures that the sound produced by the burner will be damped in the burner tube and not reverberate, amplifying the vibrations just produced.

As is shown in FIGS. 1 and 4, the mixing tube portion may at its free end be provided with two fastening flanges 11 to be connected to a gas supply tube. It is noted that the distance H indicated in FIG. 1 from the cross-section of equal width to the top of the burner bed should be so large as to ensure a straight flow of the combustion gas mixture to the burner orifices. This ensures a straight flow of the gas-air mixture to the burner bed and hence a uniform flame height and hence minimal sound production.

For the sake of completeness it is observed that instead of a burner bed formed by plane and corrugated plates or strips one could also use a burner bed of ceramic material, as is known per se in the art.

It is observed that the width of the gas outlet orifices is chosen so large that this alone will effect an $NO_x$ reduction without using the plates extending parallel to the burner axis.

To further increase the $NO_x$ reduction of the burner according to the invention, which is based on stepped combustion and flame cooling, it is possible to provide one or more additional cooling members 13 (see FIGS. 5-8 in which like elements are denoted by the same reference numerals as in the first embodiment represented in FIGS. 1-4). Such a cooling member operates in the same way as the plates 8 in that during the first step of the combustion (between the plates 8, with less oxygen than is needed) heat is withdrawn from the combustion gases. In this embodiment the cooling member 13 comprises a piece of heat-resistant fine-meshed gauze or expanded metal, which is attached to the top of plates 8 parallel to the outlet surface of the burner. The combustion gases are thus forced to flow upwards through the apertures of this cooling member and give off part of their heat-content. Only then can the secondary combustion air enter to complete the combustion.

It will be clear that further variations and modifications will readily occur to those skilled in the art without departing from the scope of the present invention.

What we claim is:

1. A low $NO_x$ atmospheric gas burner comprising at least one burner tube having a plurality of gas outlet orifices terminating in a burner bed, and a plurality of plates disposed above the burner tube within reach of a flame produced by said burner, said plates lowering a temperature of the flame and effecting a stepped combustion, characterized in that said plates (8) extend parallel to, and on opposite sides of, the orifices provided in the burner tube, said orifices being arranged in a line parallel to the burner axis, and said plates being connected directly to the burner tube substantially throughout an entire length of their lower edges.

2. A gas burner as claimed in claim 1, characterized in that each of the plates (8) is provided with at least one aperture (12) to permit the flame to transfer along the gas outlet orifices when the gas burner is ignited.

3. A gas burner as claimed in claim 1, characterized by being provided with uniformly spaced air supply holes (10) in said plates (8).

4. A gas burner as claimed in claim 1, in which the burner tube comprises a gas supply inlet and a substantially horizontal duct (3) which gradually widens away from the gas supply inlet, is shaped to deflect gas flow in an upward direction and at its outlet has a width equal to a desired width of the burner or the burner bed, the burner tube further having a constriction upstream of its outlet end, characterized in that the burner tube is provided with a distributor plate (6) at, or upstream of, said constriction.

5. A gas burner as claimed in claim 1, in which the burner tube has a bottom surface (4) that slopes upwardly, characterized in that sidewalls adjacent to the bottom surface slope outwardly from the bottom surface to a maximum width that is uniform throughout an entire length of the burner tube.

6. A gas burner as claimed in claim 5, characterized in that from a cross-section of equal maximum width the burner tube is narrowed upwardly (7) to a burner bed width.

7. A gas burner as claimed in claim 6, characterized in that a distance (H) from the cross-section of equal maximum width to a top of the burner bed is sufficiently large as to ensure a straight flow of a fuel gas mixture to the burner orifices.

8. A gas burner as claimed in claim 1, in which the burner orifices are formed by plane and corrugated plates or strips, characterized in that the height of the corrugated strips is smaller than that of the plane strips.

9. A gas burner as claimed in claim 8, characterized in that the plane strips extend vertically to above the corrugated strips.

10. A gas burner as claimed in claim 1, characterized by at least one further cooling member.

11. A gas burner as claimed in claim 10, characterized in that the further cooling member consists of heat-resistant fine-meshed gauze or expanded material.

12. A gas burner as claimed in claim 11, characterized in that the heat-resistant material is attached to said plates (8).

* * * * *